United States Patent
Kline et al.

(10) Patent No.: US 11,412,944 B2
(45) Date of Patent: Aug. 16, 2022

(54) NON-INVASIVE METHOD FOR MEASURING SOUND FREQUENCIES CREATED BY VORTICES IN A CAROTID ARTERY

(71) Applicant: CVR Medical Corporation, Denver, NC (US)

(72) Inventors: Bret Kline, Columbus, OH (US); Peter Bakema, Denver, NC (US); Young Truong, Carrboro, NC (US); Richard Finlayson, Greenville, NC (US); Orville Day, Greenville, NC (US)

(73) Assignee: CVR Medical Corporation, Denver, NC (US)

( * ) Notice: Subject to any disclaimer, the term of this patent is extended or adjusted under 35 U.S.C. 154(b) by 529 days.

(21) Appl. No.: 15/737,222

(22) PCT Filed: Jun. 15, 2016

(86) PCT No.: PCT/US2016/037621
§ 371 (c)(1),
(2) Date: Dec. 15, 2017

(87) PCT Pub. No.: WO2016/205365
PCT Pub. Date: Dec. 22, 2016

(65) Prior Publication Data
US 2018/0184918 A1    Jul. 5, 2018

Related U.S. Application Data

(60) Provisional application No. 62/175,913, filed on Jun. 15, 2015, provisional application No. 62/175,894, filed on Jun. 15, 2015.

(51) Int. Cl.
*A61B 5/0285* (2006.01)
*A61B 5/00* (2006.01)
*A61B 7/00* (2006.01)

(52) U.S. Cl.
CPC .......... *A61B 5/0285* (2013.01); *A61B 5/6822* (2013.01); *A61B 5/6823* (2013.01);
(Continued)

(58) Field of Classification Search
CPC .......... A61B 2560/0276; A61B 5/7217; A61B 5/7207; A61B 5/7221; G06F 21/31;
(Continued)

(56) References Cited

U.S. PATENT DOCUMENTS 5,727,558 A * 3/1998 Hakki ................. A61B 5/6822
600/485
5,853,005 A * 12/1998 Scanlon ................ A61B 5/113
600/459
(Continued)

FOREIGN PATENT DOCUMENTS

CN         1422591 A     6/2003
CN       101137977 A     3/2008
(Continued)

OTHER PUBLICATIONS

International Search Report dated Oct. 4, 2016 of International Application No. PCT/US2016/037621.

Primary Examiner — Sean P Dougherty
Assistant Examiner — Alexander H Connor
(74) Attorney, Agent, or Firm — Vos-IP, LLC

(57) ABSTRACT

A method for measuring sound from vortices in the carotid artery comprising: first and second quality control provisions, wherein the quality control compares detected sounds to pre-determined sounds, and upon confirmation of the quality control procedures, detecting sounds generated by the heart and sounds from vortices in the carotid artery for at least 30 seconds.

7 Claims, 8 Drawing Sheets

(52) U.S. Cl.
CPC .......... *A61B 5/6835* (2013.01); *A61B 5/7221* (2013.01); *A61B 7/00* (2013.01); *A61B 2562/0204* (2013.01)

(58) Field of Classification Search
CPC .......... G06F 21/32; H04R 1/406; H04R 1/04; H04R 1/004
See application file for complete search history.

(56) References Cited

U.S. PATENT DOCUMENTS

| | | | | |
|---|---|---|---|---|
| 6,048,319 | A * | 4/2000 | Hudgins | A61B 7/04 600/528 |
| 6,662,032 | B1 * | 12/2003 | Gavish | A61B 5/486 600/323 |
| 9,226,726 | B1 * | 1/2016 | Semmlow | A61B 7/04 |
| 9,750,461 | B1 * | 9/2017 | Telfort | A61B 5/02416 |
| 2002/0143260 | A1 * | 10/2002 | Ogura | A61B 5/022 600/500 |
| 2003/0069506 | A1 * | 4/2003 | Chassaing | A61B 7/00 600/481 |
| 2003/0135127 | A1 * | 7/2003 | Sackner | A61B 5/6805 600/536 |
| 2004/0249293 | A1 * | 12/2004 | Sandler | A61B 7/00 600/481 |
| 2005/0038360 | A1 * | 2/2005 | Shertukde | A61B 5/02007 600/586 |
| 2005/0119573 | A1 * | 6/2005 | Vilenkin | A61B 5/02007 600/450 |
| 2005/0123146 | A1 * | 6/2005 | Voix | H04R 25/70 381/60 |
| 2005/0234349 | A1 * | 10/2005 | Pravica | A61B 7/045 600/481 |
| 2006/0093192 | A1 * | 5/2006 | Bechtel | G06K 9/00013 382/126 |
| 2007/0043300 | A1 * | 2/2007 | Koblanski | A61B 5/1126 600/527 |
| 2007/0049848 | A1 * | 3/2007 | Koblanski | A61B 5/024 600/587 |
| 2007/0276270 | A1 * | 11/2007 | Tran | A61B 5/002 600/508 |
| 2008/0039733 | A1 * | 2/2008 | Unver | A61B 7/00 600/528 |
| 2008/0154140 | A1 * | 6/2008 | Chang | A61B 5/6822 600/500 |
| 2008/0287763 | A1 * | 11/2008 | Hayter | A61B 5/1473 600/365 |
| 2010/0016840 | A1 * | 1/2010 | Stahmann | A61B 5/0028 606/1 |
| 2010/0145210 | A1 * | 6/2010 | Graff | A61B 7/04 600/528 |
| 2010/0166228 | A1 * | 7/2010 | Steele | H04R 3/00 381/113 |
| 2011/0208009 | A1 * | 8/2011 | Fu | A61B 7/04 600/300 |
| 2012/0232427 | A1 * | 9/2012 | Bakema | A61B 7/04 600/586 |
| 2013/0131465 | A1 * | 5/2013 | Yamamoto | A61B 5/7271 600/301 |
| 2014/0058264 | A1 * | 2/2014 | Baym | A61B 8/429 600/447 |
| 2014/0128754 | A1 * | 5/2014 | Luna | A61B 5/7278 600/500 |
| 2014/0194740 | A1 * | 7/2014 | Stein | A61B 8/0808 600/455 |
| 2014/0343392 | A1 * | 11/2014 | Yang | A61B 5/04082 600/393 |
| 2015/0051473 | A1 * | 2/2015 | Huang | A61B 5/0095 600/407 |
| 2015/0150505 | A1 * | 6/2015 | Kaskoun | A61B 5/684 600/300 |
| 2015/0272503 | A1 * | 10/2015 | Molden | A61B 5/0082 600/386 |
| 2016/0030009 | A1 * | 2/2016 | Hoelscher | A61B 8/481 600/458 |
| 2016/0113618 | A1 * | 4/2016 | Su | A61B 7/003 600/586 |
| 2016/0121737 | A1 * | 5/2016 | Henningson | H02J 13/00002 320/109 |
| 2016/0158546 | A1 * | 6/2016 | Fredelake | G10L 25/78 607/57 |
| 2016/0205568 | A1 * | 7/2016 | Loverich | H04W 52/0245 370/252 |
| 2016/0206808 | A1 * | 7/2016 | Gray | A61B 5/1427 |
| 2017/0189220 | A1 * | 7/2017 | Ingimundarson | A61F 5/02 |
| 2017/0199162 | A1 * | 7/2017 | Nordstrom | G01N 29/30 |
| 2019/0125196 | A1 * | 5/2019 | Kline | A61B 5/7221 |
| 2019/0142360 | A1 * | 5/2019 | Kline | A61B 5/742 600/586 |

FOREIGN PATENT DOCUMENTS

| | | |
|---|---|---|
| WO | WO/1997/007733 A1 | 3/1997 |
| WO | WO/2008/000254 A1 | 1/2008 |
| WO | WO/2008/120154 A2 | 10/2008 |
| WO | WO/2009/037484 A2 | 3/2009 |
| WO | 2009039863 A1 | 4/2009 |
| WO | WO/2011/163509 A1 | 12/2011 |

* cited by examiner

NON-INVASIVE METHOD FOR MEASURING SOUND FREQUENCIES CREATED BY VORTICES IN A CAROTID ARTERY

CROSS REFERENCE TO RELATED APPLICATIONS

This application is a National Phase Stage of International Application No. PCT/US16/37621, filed Jun. 15, 2016, which claims the benefit of U.S. Provisional Application Ser. No. 62/175,894, filed Jun. 15, 2015, and 62/175,913, filed Jun. 15, 2015, which are hereby incorporated by reference in their entirety.

FIELD OF INVENTION

The present application is generally related to a method for measuring vortices in a carotid artery, by utilizing a Y shaped array comprising at least three sensor pods comprising a piezo element for detecting the sound of fluid flow generated by vortices through the carotid arteries, wherein said detection can be utilized to predict or determine stenosis in the carotid artery.

BACKGROUND OF THE INVENTION

Stroke is the major cause of adult neurological disability in the world [Malkoff 1997]. About eighty percent of all strokes occur from vessel blockage. Stroke is an enormous health burden on society. Ischemic Stroke is the most common cause of disability in adults and the third leading cause of mortality in developed countries [Birchall 2006; Silvennoinen 2007; Tan 2008]. Around the world, stroke causes nine percent of all deaths (1 in 11) and is the second leading cause of death [Kefayati 2013]. According to the World Health Organization, fifteen million people suffer stroke annually. Of these five million die and another five million are permanently disabled. In the United States stroke is the fifth, (1 in 19 in USA) leading cause of death affecting eight hundred thousand people annually (http://www.cdc.gov/stroke/). Ischemic stroke, occurring due to insufficient blood supply to the brain, accounts for the largest number of strokes (88%), followed by intracerebral hemorrhage (9%) and subarachnoid hemorrhage (3%) (http://www.strokeassociation.org/STROKEORG/About-Stroke/TypesofStroke/IschemicClots/Ischemic-Strokes-Clots_ UCM_310939_Article.jsp #.V17hu46TRE4).

The primary cause of Ischemic stroke is atherosclerosis, which is a long-term inflammatory disease, begins at the adluminal surface and eventually causes endothelial abnormalities. The thickening and hardening of the vessel wall eventually produces atherosclerotic plaques, which are essentially composed of lipid fibrous tissue and inflammatory cells. Progression of the plaque can lead to a narrowing of the lumen, i.e., stenosis. (The percentages of stenosis that will be quoted herein are by the NASCET standard of measuring stenosis). The superficial location of the carotids allows non-invasive methods to be used in detecting abnormal blood flow within them. Computational simulations and experimental flow visualizations both demonstrate marked differences in flow patterns distal to concentric and eccentric stenosis for moderately and severely stenosed cases [Steinman 2000]. This is one example of an important parameter for blood flow characteristics, which is dependent upon more than just the degree of stenosis.

Roughly, half of all strokes are caused by artherothromboembolism and most of these are extracranial atheromatous lesions, most often involving narrowing of the internal carotid arteries (ICAs) [Silvennoinen 2007]. Symptomatic patients with severe stenosis (70-99%) benefit from carotid endarterectomy. It has been suggested that endarterectomy could also reduce the risk of stroke from moderate (50-69%) stenosis; therefore, imaging of the carotid artery is indicated in patients with symptoms of cerebral ischemia [Bartlett 2006]. There are several methods known in the art for attempting to accurately determine the level of stenosis in an artery.

It is a well-known fact that death from stroke has declined dramatically in the US [Go 2014; Lackland 2014]. Lately stroke has been listed as the fifth leading cause of death rather than the third leading cause because more people are dying from lung cancer than from stroke. The American Stroke Association commissioned a panel of doctors (a "Stroke Council"), chosen on the basis of recent work in their respective fields of expertise, to assess what factors have been influencing the decline in stroke mortality. This Council issued its conclusions as "A statement from the American Heart Association/American Stroke Association" in 2008. The report was based upon systematic literature reviews, published clinical and epidemiological studies, morbidity and mortality reports, clinical and public health guidelines, authoritative statements, personal files, and expert opinion to summarize evidence. The document underwent extensive American Heart Association internal peer review, Stroke Council leadership review, and Scientific Statements Oversight Committee review before consideration and approval by the American Heart Association Science Advisory and Coordinating Committee. The review declares that "The decline of stroke mortality over the past decades represents a major improvement in population health that is observed for both sexes and all racial/ethnic and age groups. The major decline in stroke mortality represents a reduction in years of potential lives lost."

The remarkable decline in stroke mortality was acknowledged as one of the ten great public health achievements in the twentieth century. This decline has continued over the prior decade (2001 to 2010) and the drop in stroke mortality was again identified as one of the ten great public health achievements of the first decade of the twenty-first century. The Stroke Council report states that stroke mortality in the U.S. has been falling faster than ischemic heart disease mortality for several decades now. Medications for blood pressure control have had a larger and more immediate impact on stroke than on heart disease. Public health officials consider the lowering of blood pressure and hypertension control as the major contributors to the decline of stroke.

Also mentioned as contributing to the decline of stroke have been smoking cessation programs, improved control of diabetes and of abnormal cholesterol levels, and better as well as faster treatment. The Stroke Council concluded that efforts in hypertension control initiated in the 1970's were the most substantial influence to the decline in stroke mortality. An interesting aspect of this extensive report [Lackland 2014] is that Duplex Ultrasonograph ("DUS") is not mentioned specifically, in spite of all of its improvements over the decades. This dovetails well with the fact that DUS lacks precision in that there is an inability to distinguish between some of the various sub-classifications of stenosis from each other, and generally, the DUS devices provide results with error bars, which cross over entire decimal percentage subdivisions. As another example of this, DUS has a very high rate of variability in detecting and confirming stenosis at 50-69%, a "moderate" stenosis level, as compared to other levels of stenosis. This lack of precision and variability is concerning.

Despite the recent gains in stroke treatment, there remains a massive hole in early detection and treatment of patients before, not after, they have experienced stroke. Any stroke, even small, frequently leads to a rapid reduction in quality of life and this morbidity is especially troublesome as improved devices and scanning of patients could remove and avoid a large number of stroke occurrences, especially to patients that are generally deemed at a moderate or low risk.

There are several non-invasive methods and apparatus for use in predicting stenosis in the body, for example, through detecting arterial bruits. Bruits, the sounds heard in a stethoscope examination, are associated with strong risk factors for stroke, such as age and arterial hypertension. The bruits, comprised of turbulent sounds generally at higher frequencies than vortex-generated sounds, are due to turbulent blood flow motions distal to a stenosis. Those sounds that are due to vortex motions in the flow of blood are not heard directly in a stethoscope because their magnitude of intensity is not nearly as great. However, the presence or absence of a bruit does not necessarily predict underlying atherosclerosis; it only serves as a predictor.

The Framington study [Malkoff 1997] found asymptomatic carotid bruits in 3.5% of patients 44-54 years of age and 7% of patients in the category of 65-79 years of age. It was determined that although carotid bruits are associated with powerful predictors of stroke such as age, arterial hypertension, and diabetes mellitus, the presence or absence of a bruit does not reliably predict underlying carotid atherosclerosis. The study concluded that if patients in their study with a carotid bruit were studied with Doppler ultrasound or angiography, 60% would have underlying carotid stenosis. The study also showed that if patients with known carotid stenosis are checked for bruits, only approximately 10% had a carotid bruit ipsilateral to the stenosis. Bruits therefore were unreliable to determine whether there was carotid disease and if present, the extent of the disease. Other studies concerning the relationship of bruits to carotid atherosclerosis have reached similar conclusions, that bruits are not dependable signs of the existence of carotid atherosclerosis nor if present, of the extent of the disease or percent occlusion of the artery.

Phonoangiography Method.

Phonoangiography is a method, which depends upon a frequency (spectral) analysis of the turbulent sound distal to an arterial stenosis. Initially proposed in 1970 [Lees et. al., 1970; Duncan et. al., 1975], with many publications concerned with the method throughout the following years, it strives to establish a clinical diagnosis of the extent of carotid stenosis made non-invasively by quantitative analysis of the frequency spectrum of a bruit. Frequencies under 50 Hz are discarded. The intensity of sound increases with frequency until it reaches (generally) a single discrete maximum beyond which it falls off with a characteristic steep slope. The key element in the method is the detection of a frequency peak that is generally a single peak. The frequency at which the peak amplitude occurs is called the "break" frequency $f_0$. It is related by a succinct empirical formula to the estimated degree of stenosis. In carotid and femoral human arteries, the break frequency appears between 800 and 1000 Hz. In dog aorta, it occurs between 1000 to 1500 Hz. Over a span of at least 40 years the method, thought to be a promising non-invasive method for determining carotid stenosis, has never been able to successfully launch a device to compete with Doppler Ultrasound nor other non-invasive methods.

Doppler Ultrasound Method

Duplex Ultrasonograph (DUS) is generally considered the primary non-invasive screening procedure for evaluation of Internal Carotid Artery (ICA) stenosis and is widely used in clinical practice to select patients for angiography or some other non-invasive method, or for endarterectomy itself [Jahromi 2005]. Angiography, however, is resource intensive and has an inherent risk of morbidity and mortality that decreases the potential benefit of carotid endarterectomy. Consequently, some clinicians have advocated endarterectomy on the basis of DUS findings alone, or in combination with Magnetic Resonance Angiography (MRA) or Computed Tomography Angiography CTA. Jahromi concluded that "measurement properties vary widely between laboratories and the magnitude of the variation is clinically important. Data show that random error is prevalent." "A DUS report should include a predicted stenosis that is based on a complex relationship between velocities and degree of stenosis, and that is device specific." Jahromi discusses the issue of threshold selection, calibration of data, and the problem associated with which thresholds provide the optimal combination of sensitivity and specificity. It states that such issues are even more important for asymptomatic than for symptomatic patients since the risk benefit ratio is more marginal for the former. It warns that failure to maintain high specificity and high positive predictive value exposes patients without significant stenosis to certain risks.

Though standards have been adopted by most ultrasound labs since that [Jahromi 2005] article, a more recent article [Alexandrov 2012], explains that "the need to arrive at some consensus and to recommend a more unified approach, led to the European publication by de Bray and Glatt in 1995 [De Bray, et. al., 1995], the Society of Radiologists in Ultrasound Multi-Disciplinary Consensus Panel in 2003 [Grant, et. al., 2003], and a United Kingdom working group document in 2008 [Oates, et. al., 2009]." The entities "managed to agree on a set of criteria to grade a . . . carotid artery stenosis . . . but its acceptance is far from universal. This new consensus . . . codifies a sonographic diagnosis using a combination of [several] criteria . . . . These guidelines combine criteria more formally than most others have [done] before." The authors continue: "As one increases the number of criteria to define categories of disease . . . what happens to sensitivity and specificity? Will the screening test perform any better? This . . . may lead to better positive predictive values, but it can potentially reduce sensitivity dramatically . . . . A criterion chosen for its high specificity without a sufficiently high sensitivity may be acceptable if analyzed alone but may cause unanticipated results when combined with other criteria."

Other groups have recommended performing a DUS test twice, or combining a DUS test result with the estimation of degree of stenosis by another non-invasive method. For example, in a 2003 article by a panel of authors reflecting the consensus opinion of the conference attendees of The Society of Radiologists in Ultrasound Consensus Conference [Grant, et. al., 2003], the authors proposed a list of five recommendations for all ICA exams, only the first of which we mention here, which is to combine the results of three Doppler methods, namely, the grayscale, color and spectral Doppler results. The authors state the conference consensus opinion that "the conclusions [of the test] should state an estimated degree of ICA stenosis as reflected in these [five] categories." Further, the panel of authors representing the conference consensus "identify several important unanswered questions meriting future research." Of course, while such increased specificity and confirmation is wonderful in theory, implementation of such a recommendation would dramatically increase expenses that would be involved for an exam that is performed according to these recommendations.

Some reasons that such a conference was held are reiterated in a 2009 article [Chappell, et. al., 2009] as reported by authors from various English and Scottish Universities and Hospitals, including Departments of Radiology, Medicine for the Elderly and Stroke Service, Cardiovascular Research Centre, Department of Vascular Surgery, Department of Clinical Neurology, and National Hospital for Neurology and Neurosurgery. Original data was analyzed upon which 41 studies were based that qualified under the high standards used in this study, comprising 2541 carotid arteries. The study was conducted in order to "find clinically relevant estimates of the accuracy of noninvasive imaging—DUS, CTA, MRA, and Contrast-Enhanced MRA (CEMRA) . . . in diagnosing both severe and moderate symptomatic [as well as asymptomatic] carotid artery stenosis . . . and to estimate the probability of agreement between two noninvasive tests." Original data sets were requested in order to "make direct comparisons of noninvasive tests, or to determine the accuracy of noninvasive tests in combination. [Several factors as well as] probable publication bias leading to overestimation of true sensitivity and specificity . . . for informing clinical practice". The study concludes that the sensitivity of DUS for symptomatic patients (most of the 2541 total) [using the Nascet standard] was: 83% for severe (70 to 99%) stenosis, 31% for moderate (50 to 69%) stenosis, and 52% for no or mild (0 to 49%) stenosis. For asymptomatic patients, the sensitivity results were respectively, for the three categories of classification: 67%, 40% and 88%. For all patients combined, DUS sensitivity was respectively, 82%, 34% and 74%. Specificity of DUS for symptomatic patients was, respectively, 54%, 84% and 96%; for asymptomatic patients—93%, 90% and 83%. For all patients, DUS specificity was: 76%, 85%, and 94% respectively. These values are particularly concerning based on the low values of sensitivity and specificity for the moderate degree of stenosis in particular, but they also remain concerning for all levels of detection. Indeed, these numbers reflect that there is a high level of ambiguity and uncertainty in performing such important tests.

This uncertainty and ambiguity is further corroborated when two tests were performed back-to-back, and wherein agreement for the percent stenosis was surprisingly low, even when performing the same test. Comparison of two non-invasive tests: DUS followed by DUS: 86% agreement on severe grade of stenosis, 58% agreement on moderate degree of stenosis, and 91% for mild or no stenosis. DUS followed by CEMRA: 80% agreement on severe grade, 43% for moderate grade, and 66% for mild/no grade of stenosis. Again, especially low values for moderate degree of stenosis.

An article written later [Beach, et. al., 2012] whose authors are at the University of Washington Medical Center, Department of Surgery, and Applied Physics Laboratory, compares DUS to anatomic x-ray contrast angiography. Wherein, "Exam Disagreement for Angiographic 50% to 69% Classification" places DUS vs angiography at 55 to 62% when DUS is based upon one parameter, either Systolic Velocity, Diastolic Velocity or Velocity Ratio between the two. Therefore, while DUS is usually the first imaging method for carotid arteries [Titi, et. al., 2007], it remains unreliable.

That said, DUS remains prevalent because it has many advantages such as, it is fast, taking on the order of 15 or 20 minutes; it is non-invasive; it does not use dyes or ionizing radiation by x-rays; and is widely available (DUS devices are widespread in use throughout the world). However, a confirmatory imaging method is likely necessary if an intervention is considered and certainly required if the degree of stenosis remains undetermined by DUS [Grant, et. al., 2003]. Therefore, as opposed to invasive procedures, suggestions of three types of Doppler, grayscale, color and spectral DUS may be warranted in some circumstances in order to provide better accuracy for patient evaluation. This however raises the expense and time for a test but still manifests frequent difficulties in determining whether or not the stenosis is below or above seventy percent, as well as when categorizing a moderate stenosis (from fifty to sixty nine percent stenosis).

Additional devices and procedures are detailed by Semmlow and Rahalkar "Acoustic Detection of Coronary Artery Disease" [Annu. Rev. Biomed. Eng. 2007; 9:449-69] provides a detailed look at several listening devices and discusses the failure of each of said devices. However, as detailed therein, there remains a significant hurdle in finding methods and devices for use within those methods that are able to better identify and quantify stenosis in the carotid artery.

Some US patents and publications have attempted to describe new methods for determining stenosis. For example, in U.S. Pat. No. 7,621,875 ('875), the inventors proposed several strategies to effectively measure sounds from the arteries to estimate stenosis. However, the '875 patent was not able to eliminate enough of the noise present to create any meaningful data—indeed, it may be that the '875 was not even sure of what data should be identified. Two, the device was not able to determine the correct signal of what an artery with or without stenosis should sound like. Therefore, the '875 proposed to, but was unable to, generate an estimation for stenosis in an artery.

Indeed, the '875 suggested to generate a complex frequency grid of frequencies and associated lifetimes of the obtained acoustic signals and then to generate a predictive model of complex frequencies associated with peak-perturbation acoustic signals attributed to boundary perturbations in vivo that occur with early stage arterial disease. However, the generation of an unknown frequency grid and associated lifetimes was generally noise, without more, and there was a complete inability to determine or predict stenosis based on this frequency grip collected according to the '875.

Prior work by A. O. Borisyuk provided a disclosure of determining peak sound frequencies in the carotid artery. A summary to his work is as follows. Wall pressure fluctuations in rigid and elastic pipes behind a local axisymmetric narrowing are studied. A sharp increase in their root mean-squared (rms) level in a finite region immediately downstream of the narrowing, leading up to a pronounced maximum upstream of the point of j et reattachment, is found. Approximate estimates both for the distance from the narrowing to the point of maximum rms pressure and for the rms magnitude at this point are obtained. Inspection of the wall pressure power spectrum reveals the presence of low-frequency maxima. The maxima are found to be associated with the large-scale eddies in the regions of separated and reattached flow, and their frequencies are close to the characteristic frequencies of the eddies' formation. These maxima are the main distinguishing features of the spectrum under investigation compared to the power spectrum of the wall pressure fluctuations in a fully developed turbulent flow in a pipe without narrowing. A comparative analysis of the data for rigid and elastic pipes shows that changes in the pipe wall bending stiffness cause alterations in the flow structure near the wall and the corresponding redistribution of flow energy among the vortices. This results in an increase in the wall pressure amplitude and the low-frequency level of the wall pressure power spectrum, as well as the appearance of new frequency components in this domain. [Journal of Fluids and Structures 2010; 26: 658-674.] These formations, however do not measure the specific vortices as described by the present disclosure.

Therefore, while devices exist for predicting stenosis in the carotid artery, these methods use antiquated technology and lack precision necessary for effective treatment in modern medicine. Accordingly, new methods are necessary for detecting vortices in the carotid artery, wherein the measurements can be utilized for quantification and determination of stenosis or occlusion in the carotid artery.

SUMMARY OF THE INVENTION

In accordance with these and other objects, a first embodiment of an invention disclosed herein is directed to a method for detecting vortices in the carotid artery of a human patient consisting of the following steps: applying a set of three piezoelectric sensors to a patient, wherein said piezoelectric sensors are positioned on a Y shaped apparatus, positioning a first sensor on the heart and the two remaining sensors on each side of the neck of the patient, adjacent to the carotid artery; measuring and recording the sound from the first sensor and from the second and third sensors; formatting the recorded sound from analog to digital at a sampling rate of 20 kHz; graphing the sound from 40 to 1600 Hz in a power spectral density graph.

In a further embodiment, a method of measuring vortices in the carotid artery comprising a detection system comprising a base unit, an array, at least two sensing pods, a computer having software implemented therein for running the system, and a display; wherein said method comprises: performing a quality control test comprising delivering a sound from the base unit to be detected by the sensing pods stored thereupon; placing sensing pods on a patient, wherein at least one sensing pod is adjacent to the heart and one sensing pod is adjacent to a carotid artery; performing a second quality control procedure based on the sounds detected by the sensing pods; detecting and recording sounds from the sensing pods from the heart and the carotid artery with said sensing pods; formatting the recorded sound to digital and graphing sounds from 40 to 1600 Hz in a power spectral density graph.

A method for measuring sound from vortices in the carotid artery comprising: performing a first quality control procedure on at least two sensing elements, wherein said quality control procedure is performed by playing a pre-determined set of tones within a base unit, wherein said at least two sensing elements detect said set of tones and wherein said detected tones are compared to said pre-determined set of tones; performing a second quality control procedure on at least two sensing elements, wherein said second quality control procedure is performed by detecting sounds generated by the heart and by blood flow through the carotid artery; wherein said at least two sensing elements detect said sounds generated by the heart and blood flow through the carotid artery, and said detected sounds are compared to a previously recorded set of sounds corresponding to the sounds generated by the heart and blood flow through the carotid artery; and detecting sounds generated by the heart and sounds from vortices in the carotid artery for at least 30 seconds.

A further embodiment comprises wherein the sounds detected from the vortices in the carotid artery are between 40 Hz and 1600 Hz. A further embodiment comprises a further step (d) of eliminating sounds from the carotid artery that are outside of the range of 40 Hz and 1600 Hz. A further embodiment comprising a further step (e) comprising generating a power spectral density graph of the sounds from step (d). A further embodiment wherein three sensor pods are utilized to simultaneously detect sounds from the heart and carotid arteries.

In a further embodiment, the methods wherein if the comparison between said detected tones and said pre-determined tones has a variance of more than 5% relative to the amplitude or wavelength, then the sensing element needs to be replaced. And a further embodiment requires wherein if the detected sounds compared to the previously recorded sounds have a variance of more than 25% relative to the amplitude or wavelength, then the sensing elements need to be repositioned.

A method for measuring vortices produced in the carotid artery due to plaque accumulation in the artery comprising: performing a first quality control procedure on at least two sensing elements, wherein said quality control procedure is performed by playing a pre-determined set of tones within a base unit, wherein said at least two sensing elements detect said set of tones and wherein said detected tones are compared to said pre-determined set of tones, wherein if said tones are within 5% of the amplitude and wavelength, the quality control procedure is passed, wherein the quality control fails, replacement of one or more sensing elements is required; performing a second quality control procedure on at least two sensing elements, wherein said second quality control procedure is performed by detecting sounds generated by the heart and by blood flow through the carotid artery; wherein said at least two sensing elements detect said sounds generated by the heart and blood flow through the carotid artery, and said detected sounds are compared to a previously recorded set of sounds corresponding to the sounds generated by the heart and blood flow through the carotid artery, wherein detected sounds within 25% of the previously recorded set of sounds based on amplitude and wavelength confirms an appropriate position, and wherein detected sounds greater than 25% require repositioning of one or more of the sensors; and detecting sounds generated by the heart and sounds from vortices in the carotid artery for at least 30 seconds.

In preferred embodiments, the methods utilize three sensor pods, wherein the detection of sounds generated by the heart and sounds from the vortices in the carotid artery are detected simultaneously by the three sensor pods at between 40 and 1600 Hz.

A system for measuring vortices in the carotid artery comprising: a computer, a microprocessor and memory attached thereto capable of running software, a software program, a base unit comprising at least one speaker, and an array comprising at least three sensor pods, wherein said sensor pods comprising a piezoelectric unit suitable for detecting sounds in the range of 40 Hz to 1600 Hz; wherein said array and sensor pods are positioned within a cradle of said base unit, and wherein said software generates a set of pre-determined tones through said at least one speaker and wherein said pre-determined tones are detected by said sensor pods and said software compares the detected sounds to the generated pre-determined tones to confirm that each sensor pod is accurately detecting said pre-determined tones within 5% of the Hz and amplitude of the pre-determined tones; wherein said array and sensor pods are placed onto a patient and wherein one sensor pod is placed adjacent to the heart and the second and third sensor pods are placed adjacent to the left and right carotid arteries; wherein a second quality control procedure is performed for 15 seconds, wherein the sensor pods detect sounds from the heart and the carotid arteries and the software compares the detected sounds to a pre-determined set of sounds corresponding to the heart and sounds generated by fluid flow in the carotid arteries; detecting sounds from the heart and the carotid arteries for between 30 to 120 seconds; and down sampling the detected sounds from analog to digital at a sampling rate of 20 kHz; and, removing sounds from the digital outside of the 40 Hz to 1600 Hz range.

A further embodiment is directed to a method for determining stenosis of the carotid artery in a human patient consisting of a first step of placing a sensing device comprising an array and three sensing elements onto the patient, wherein a first sensing element is placed near the heart and the two remaining sensing elements are placed adjacent to the carotid arteries; the sensing elements then measure sounds from each of the three sensing elements, resulting in sound from three channels; wherein the sound is measured in analog and modified to digital format via down sampling the detected sounds at a sampling rate of 20 kHz; wherein the digital sounds between 40 Hz and 1600 Hz are maintained and a power spectral density analysis is performed; wherein the power spectral density graph reveals peaks related to the vortices generated due to stenosis in the carotid artery; wherein said power spectral density graph provides for a determination of stenosis in the carotid artery.

A further embodiment is directed to a method for detecting stenosis in the carotid artery of a human patient consisting of: applying a set of three piezoelectric sensors to a patient, wherein said piezoelectric sensors are positioned on a Y-shaped array, positioning a first sensor on the heart and the two remaining sensors on each side of the neck of the patient, adjacent to the carotid artery; detecting and recording the sound from the three sensors simultaneously; formatting the measured sound from analog to digital via down sampling the data at 20 kHz; graphing the digital sound from a range of 40 Hz to 1600 Hz in a power spectral density graph and removing all other sounds; and determining the level of stenosis based on the graphical representation of the power spectral density graph.

A further embodiment is directed to a method of quantifying stenosis in the carotid artery using a Y-shaped array having three sensors, consisting of: applying a first sensor attached to the leg of the Y-shaped array, to a position proximate to the heart; applying a second sensor to a position proximate to the left external carotid artery, and applying the third sensor to a position proximate to the right external carotid artery; utilizing the sensors recording the acoustic sounds at 40 to 1600 Hz from the heart and the right and left carotid arteries; transforming the acoustic sounds into digital; plotting a graph of the power spectral density from the recorded sounds, and determining the level of stenosis in the carotid artery.

A further embodiment is directed to a method for detecting stenosis in the carotid artery of a human patient consisting of the following steps: applying a set of three piezoelectric sensors to a patient, wherein said piezoelectric sensors are positioned on a Y shaped apparatus, positioning a first sensor on the heart and the two remaining sensors on each side of the neck of the patient, adjacent to the carotid artery; measuring the sound from the first sensor and from the second and third sensors; formatting the measured sound from analog to digital; removing noise from the data; graphing the sound from 40 to 1600 Hz in a power spectral density graph; and determining the level of stenosis based on an algorithm to the data from the power spectral density graph.

A further embodiment is directed to a device suitable for measuring vortices in the carotid artery comprising: a base unit, an array and three sensor pods; wherein the base comprises a speaker engaged to a computer system and wherein the array is a Y shaped array having disposed on each branch a sensor pod; wherein each sensor pod comprises a piezoelectric unit capable of detecting and transmitting sounds between 40 and 1600 Hz to the computer system for detection of vortices in the carotid artery.

DETAILED DESCRIPTION OF THE PREFERRED EMBODIMENTS

Figure 1:
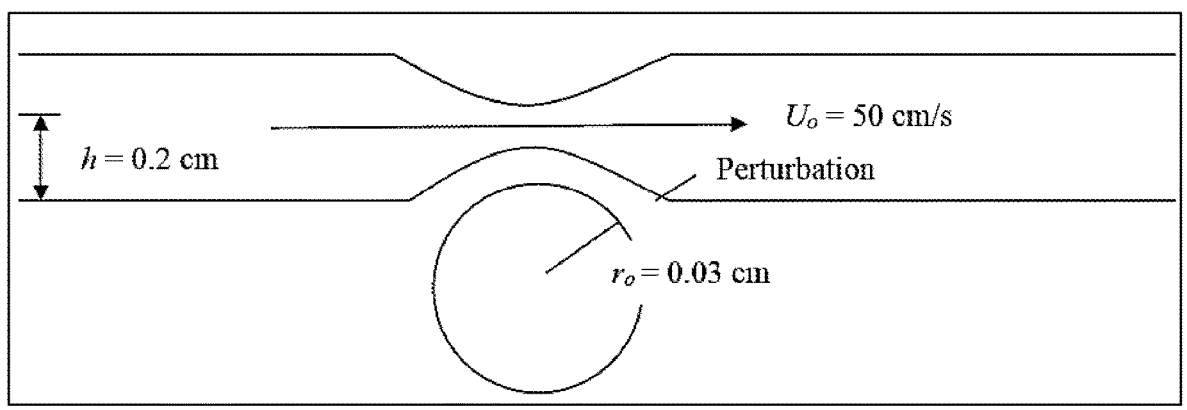
FIG. 1 depicts a representation of a partially occluded artery and depicts the formation of vortices, which are measured herein.

The embodiments of the invention and the various features and advantages thereto are more fully explained with references to the non-limiting embodiments and examples that are described and set forth in the following descriptions of those examples. Descriptions of well-known components and techniques may be omitted to avoid obscuring the invention. The examples used herein are intended merely to facilitate an understanding of ways in which the invention may be practiced and to further enable those skilled in the art to practice the invention. Accordingly, the examples and embodiments set forth herein should not be construed as limiting the scope of the invention, which is defined by the appended claims.

As used herein, terms such as "a," "an," and "the" include singular and plural referents unless the context clearly demands otherwise.

As used herein, the terms "stenosis determination" or "stenosis quantification" mean use of data gathered from vortices in the carotid artery, which is then used to predict the amount of stenosis in the carotid artery. Applicants recognize that absent a more invasive procedure including actual physical calculation or visualization of the artery means that the determination or quantification remains an estimate based on the data provided through the methods described herein.

As used herein, the term "SDD" refers to a stenosis detection device, which comprises two or more sensor pods, with at least one pod adjacent to the heart and at least one pod adjacent to an artery, typically the carotid artery. Certain devices further comprise an array, which, support and place the sensor pods in appropriate locations for detection. Certain embodiments further comprising a base unit that provides a mechanism to charge the sensor pods and perform quality control measures. The SDD further comprises a computer having a program thereto for performing the quality control methods and for processing and capturing data detected by the sensor pods.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

In the field of medicine, the flow of blood through the circulatory system is of particular interest as stenosis, a constriction or narrowing of a blood vessel, often leads to stroke, heart attack, or other medical emergencies. The flow of blood and other fluids in the body creates several sounds, many of which have a telltale signature. Doctors frequently utilize a stethoscope to listen to these sounds in the body that are discernable with this hand-held device and listen for such known signatures for checking on patients. However, there are further, faint sounds that are not discernable with a hand-held stethoscope and require further devices and methods for detecting vortices and for stenosis determination and quantification.

To date, the ability to quickly assess blockage in the carotid artery is performed by one of several devices including DUS systems. DUS is not an acoustic listening device, like those utilized in the methods described herein. Indeed, DUS systems require specialized training and are susceptible to high variability when used by even the most highly trained technicians. Indeed, the Doppler systems lack precision to determine the percent occlusion of the carotid artery within a few percentage points. This poses problems as such DUS systems have both unacceptably high rates of false positive and false negative reports. In the case of false positive reports, this often subjects a patient to further testing, including MRI scans or, in some cases, invasive surgeries. In the case of false negative reports, the incorrect assessment is potentially even more damaging, as a false negative outcome results in a patient potentially missing treatment for stenosis.

Furthermore, DUS systems, as imaging devices cannot detect, amplify, and record sounds in the carotid artery and the heart. The SDD device described herein and the methods disclosed provide a novel mechanism for detecting vortices in the carotid artery generated by plaque buildup within the arterial walls.

In preferred embodiments of the present disclosure, methods are utilized in conjunction with appropriate medical devices to measure coherent flow structures called vortices. Vortex motion in the post stenotic region is considered a secondary flow because it is much harder to measure than turbulent motions and generates sound of much lower intensity than that produced by turbulence. Turbulence is always present even in entirely healthy arteries unlike the vortex motion that is measured by the methods described herein. The secondary motions occur due to bends and bifurcations in the artery, the same type of things that create vortices in the blood flow.

The carotid artery has a branch that feeds two main areas in the head. One main branch going to the brain and the other branch going to the face. The area is tested where the carotid artery branches into these two areas. Thus depending if there is stenosis in one branch or two, the result can lead to multiple sounds being picked up. Because these sounds/vibrations are at such a low level, it is necessary to properly filter the sounds and to plot only the power spectral density with regard to a selected range between 40 and 1600 Hz. This range provides sufficient data so that the system can plot peaks and determine the percent stenosis in the body.

For example, FIG. 1 depicts a representation of a narrowing of an artery and the mechanism for generation of vortices thereto. The vortices constitute a coherent disturbance causing oscillations at the artery wall of discrete frequencies due to circumferential velocities perpendicular to the axially directed velocities. There is a spread or broadening of frequencies surrounding the discrete ones in a nearly bell curve shape in the intensity signal once turbulent noise has been substantially cut down in intensity. The oscillations in blood motions that are circumferential as well as some of the intensity of radial oscillations, which are perpendicular to the wall, are associated with vortex motions.

A key issue in hearing the low intensity sounds is utilizing a device that is sensitive enough to accurately detect sounds (from vortex motion) with the range of 40 Hz to 1.6 kHz and amplitude corresponding to the low intensity sounds generated by the vortices. The piezoelectric sensors in the described sensor pods can detect sounds of range of about <40 Hz to 28 kHz, though the sounds at issue are typically found in the 40 to 1600 Hz range and more particularly in the 60 to 1200 Hz range. Normal blood flow in a healthy patient causes certain sounds that are detectable by the device. Patients that have stenosis in the carotid arteries will often have another 2 or 3 additional sounds that can be picked up by our device. Depending on the amount of stenosis and how many stenosed areas, the sound will change and these changes can be heard, quantified, and ultimately utilized to determine percent stenosis.

The methods described herein preferably utilize a Y shaped device having attached, three sensor pods, wherein the sensor pods are capable of measuring the vortices in the carotid arteries by detecting sounds at the heart and at both the left and right carotid arteries. The device is directly sensitive to coherent flow structures called vortices, which seem to be directly related to the causes of plaque build-up; therefore signs of flow having a direct correlation with blockage and stroke prediction. The device is operator independent with analysis and display of results being entirely computer generated. This is in direct contrast to devices such as DUS, which is operator dependent.

Despite the prevalence of devices on the market that purport to determine stenosis in the carotid arteries, a method and device for use in appropriate methods for detection of these low intensity vortices has not been previously disclosed. Accordingly, a completely new type of listening device is necessary to enact the specificity necessary for effective sensing and measuring of vortices to generate data of sufficient specificity, wherein the data can ultimately be utilized in downstream processing for determining or identifying occlusion or stenosis in the carotid artery. Only after numerous iterations were we able to make a device having the necessary features to detect the sounds we were seeking and to block and remove sounds unrelated to the vortices, which we are measuring. Furthermore, the methodologies necessary for implementing and using such a device provide for new and useful methods of using the detected sounds from the vortices in the carotid artery to predict stenosis.

Figure 2:
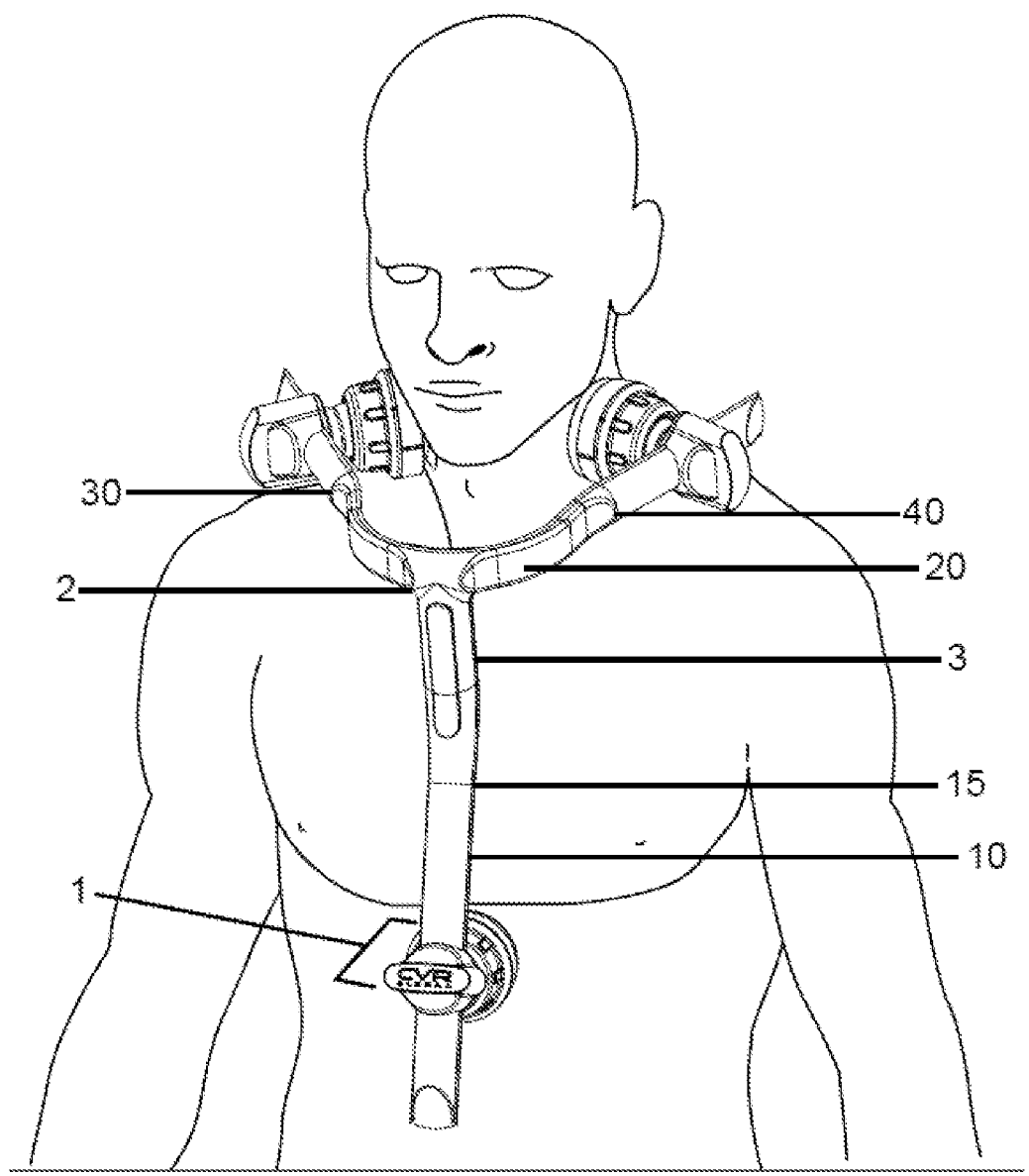
FIG. 2 depicts a carotid stenosis sensor placed on a patient for detecting and measuring vortices at the carotid artery.

FIG. 2 depicts an array placed on a representative patient. The array utilized in detecting stenosis utilizes a Y-shaped array with three attached piezoelectric units. Attached to one end of the piezoelectric unit is a sensor pad made of a gel material, such as silicone or another mixture of viscoelastic materials. Once the sensor pads are placed on the body, an operator of the device engages the device to begin recording sounds from each of the sensors placed on or adjacent to the body.

As shown in FIG. 2, the array has a general "Y" shape comprising a stem 10, as and two arms 30 and 40. Each of the stem 10 and the left arm 40 and right arm 30 can support a sensor. The sensor pods 1, positioned on each of the arms 30, 40, are positioned proximate to the carotid arteries during a test, and a third sensor pod 1, positioned on the stem 10, is generally positioned near the sternum/heart.

The upper two branches 30 and 40 or arms are flexibly connected to a shoulder 20 to allow for adjusting the sensors to properly position each sensing element on the carotid arteries regardless of the size and shape of the patient being tested. In this regard, as depicted in FIGS. 1A and 1B the upper two branches 30, 40 are biased inward toward each other as attached to the shoulders 20. The angle opening at the shoulder 20 is between about 90° and 145°. The angle can be easily modified, as each of the left and right arms 30, 40, and specifically the shoulder 20, are sufficiently flexible to be modified to fit a patient. The arms 30, 40 have a base, unflexed position, and can be bent/flexed outward or compressed inward, to fit patients needing a different orientation or width.

The shoulder 20 is attached to the neck vertex 2, which is thereafter connected to the neck 3, which is connected to a stem vertex 15, which is connected to the stem 10. The neck 3 and stem 10 connect at the stem vertex 15 at an angle of about 125° to about 175°. The positioning of the neck 3 and stem 10 allows for the bottom sensor pod 1 to be properly positioned over or near the heart.

Figure 4:
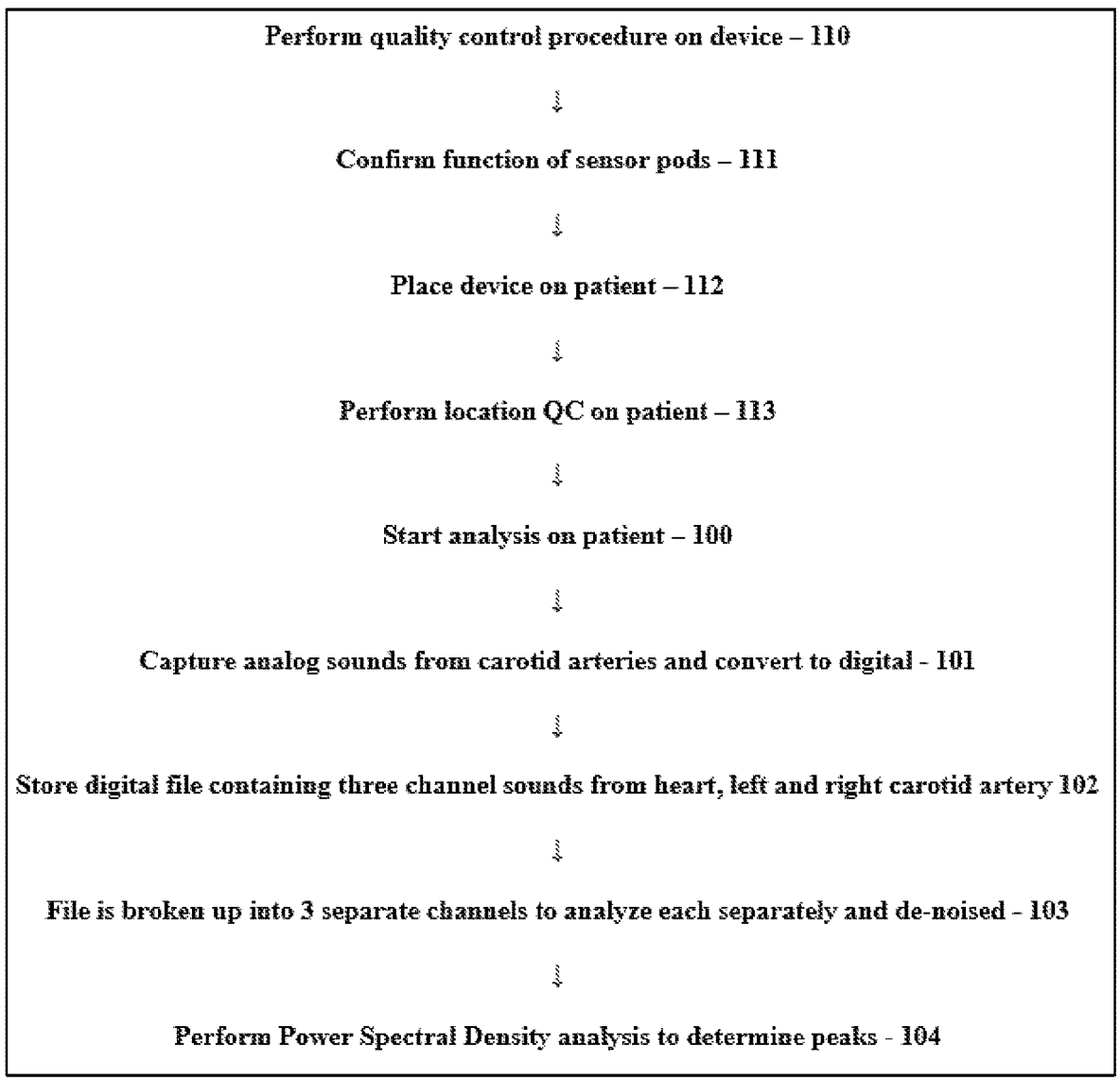
FIG. 4 depicts a flow chart showing a method for measuring vortices in the carotid artery.

Ultimately, the neck 3 connects to the neck vertex 2, which connects to the shoulder 20, which connects to the left and right arms 30 and 40. Each arm 30, 40 comprises a notched opening 31 and 41 as shown in FIG. 4, which aids in reducing weight and provides the appropriate modulus for bending the plastic material to fit different sized patients. Furthermore, the notched opening provides a track-like feature to allow for the sensor pods 1 to slideably engage and move along the arms 30, 40 and the stem 10.

The plastic that is utilized is selected based at least in part on strength, stability, and ease of use. Therefore, preferred materials include polypropylene or other plastic materials. Such materials can be manufactured via any number of means, including printed, molded, extruded, or formed by one of ordinary skill in the art. The components can be manufactured separately and connected together or manufactured as a single piece.

The sensor array as depicted in FIG. 2 and described and used in the methods herein, is a highly sensitive acoustic capturing device, capable of receiving sound waves internal to the body that flow at a frequency range of <40-1600 Hz. The Y-shaped array is adjustably configured to account for the anatomical differences between individuals, to filter external noise and amplify the sound signature emitting passively from the human body. The sensor pods 1 attached to the sensor array comprise a sensitive piezoelectric detection unit that is suitable for detecting and transmitting sounds to a computer system wherein said sounds can be captured and stored for processing.

In accordance with one embodiment, the sensor elements in collaboration with the software or application running on a PC or main computing unit, takes three readings simultaneously from the right and left carotid arteries in the neck and from the heart just below the sternum, calibrates the sound signature, filters and then digitizes data for analysis. A shielded cable transmits the signals to the main computing unit. In further embodiments, signals and data can be transmitted via other transmission means, including wireless, Bluetooth, or other suitable data transmission mechanisms.

The array is adjustably designed to fit the majority of adult persons and may be held by the patient or a third person, when performing a carotid artery test. In a preferred embodiment, the array, when placed on the patient, imparts sufficient pressure on the patient so as to achieve a measurement of sufficient quality to accurately determine stenosis, all the while limiting the pressure applied to the carotid artery. The goal is for there to be sufficient pressure to assist in positioning the sensing elements, and maintaining their position for about 2-3 minutes during a test, but not such pressure as to significantly impact the shape and size of the carotid artery being assessed. Indeed, as a whole, the array and the sensing elements are designed to be a passive test that is non-emitting, non-invasive, and is configured so that anyone can conduct the test without requiring certification.

Figure 3:
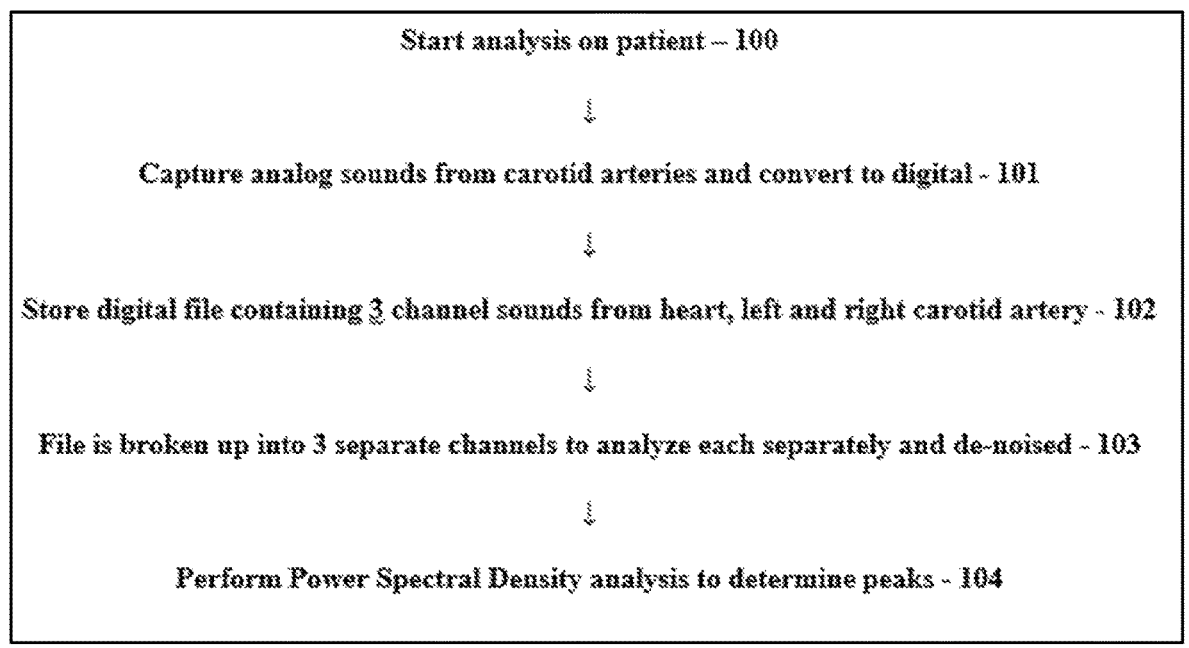
FIG. 3 depicts a flow chart showing a method for measuring vortices in the carotid artery.

In a preferred embodiment, as depicted in FIG. 3, a method of detecting vortices in the carotid artery comprising starting analysis on the patient 100. By this step, the sensor pods 1 are placed on the patient and an operator engages the CDD to begin recording sounds from each of the sensor pods 1. The sounds are captured in analog from the carotid arteries and from the heart and converted to digital 101, by down sampling at a sampling rate of 20 kHz. The next step comprises the system storing the down sampled digital file corresponding to the heart, left and right carotid arteries 102. The file is broken into three separate channels and de-noised and analyzed separated 103. Finally, a power spectral density analysis is performed and peaks determined 104.

Thus, an appropriate method comprises the following steps: (1) placing a detection device on the patient, wherein the detection device comprises a Y-shaped array 2 and attached to each of the stem 10 and two arms 30, 40 of the array is a sensing pod 1 suitable for detection of low frequency and low intensity sounds produced by the vortices. A following step comprises (2) placing the stem sensing pod adjacent to the heart, and placing the left and right arm sensing pods adjacent to the left and right carotid artery. After placing the sensing pods on the appropriate locations, (3) measuring sounds emitted from the heart and from the vortices in the carotid artery. Finally, (4) capturing the sounds in analog format and converting the sounds to digital. Therefore, certain software is necessary to perform these specific tasks and to capture and convert the data from the device and to organize the data and generate spectral density graphs that display the data where it can be further utilized, in certain embodiments, to predict stenosis.

In further embodiments, for example, as depicted in FIG. 4 an embodiment comprises additional steps that are necessary to ensure that the device is properly functioning by performing a quality control procedure. These additional steps include: performing a quality control procedure on the device 110. This quality control procedure 110 confirms that the sensor pods are functioning correctly 111. The device can then be placed on a patient 112 and a further quality control procedure 113 is performed to ensure that the device is properly located on the patient. Then the analysis 100 can begin on the patient.

In a preferred embodiment, the invention is directed to methods of determining proper placement of sensing pods from a stenosis detection device (SDD). The SDD comprises several components that are necessary for proper detection of stenosis in the carotid artery, or other artery or vessel as is appropriate. The SDD comprises base unit, a computer, a display, and at least the two sensor pods.

Figure 7:
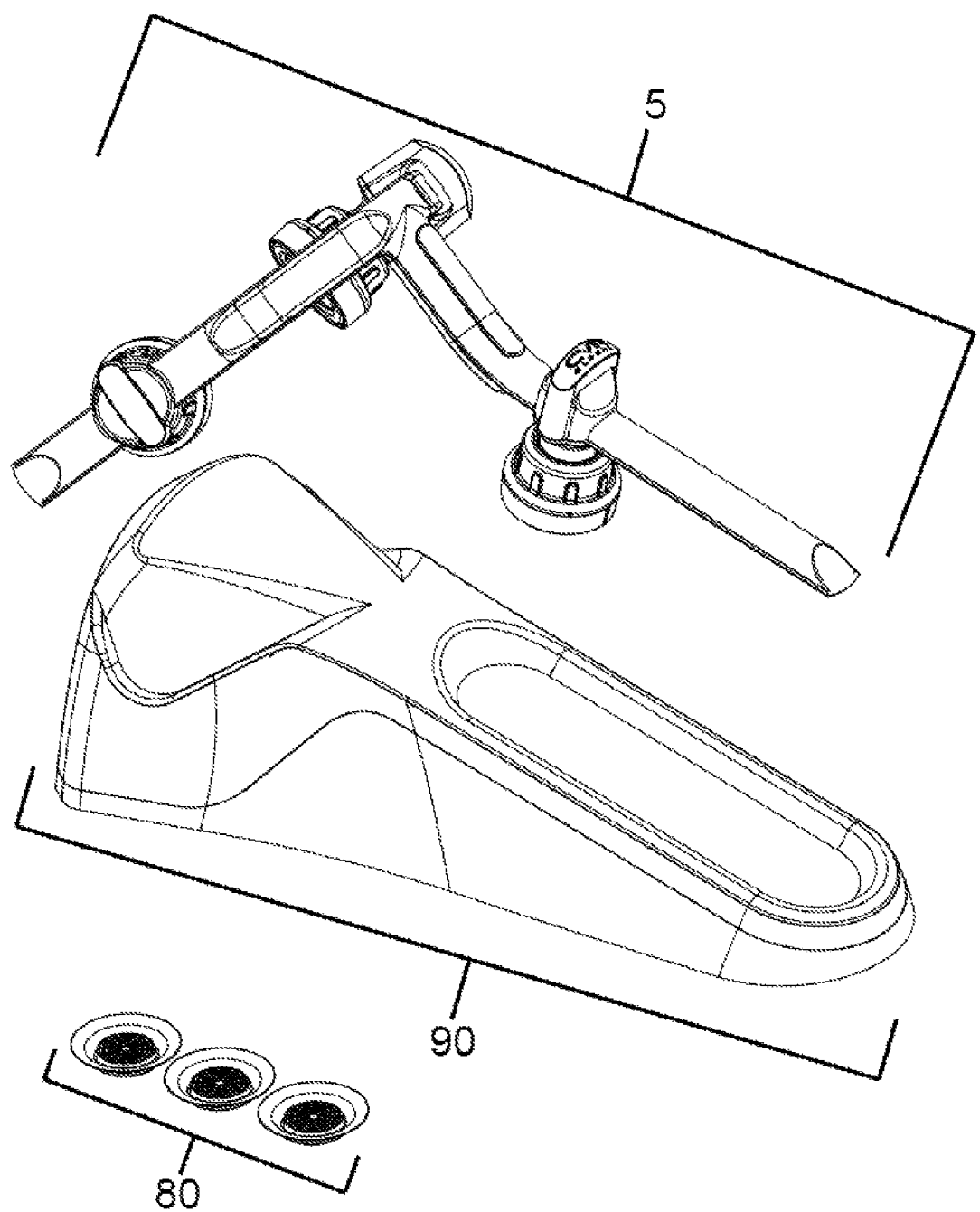
FIG. 7 depicts an embodiment of a sensor array, a sensor base, and three sensor pads.
Figure 8:
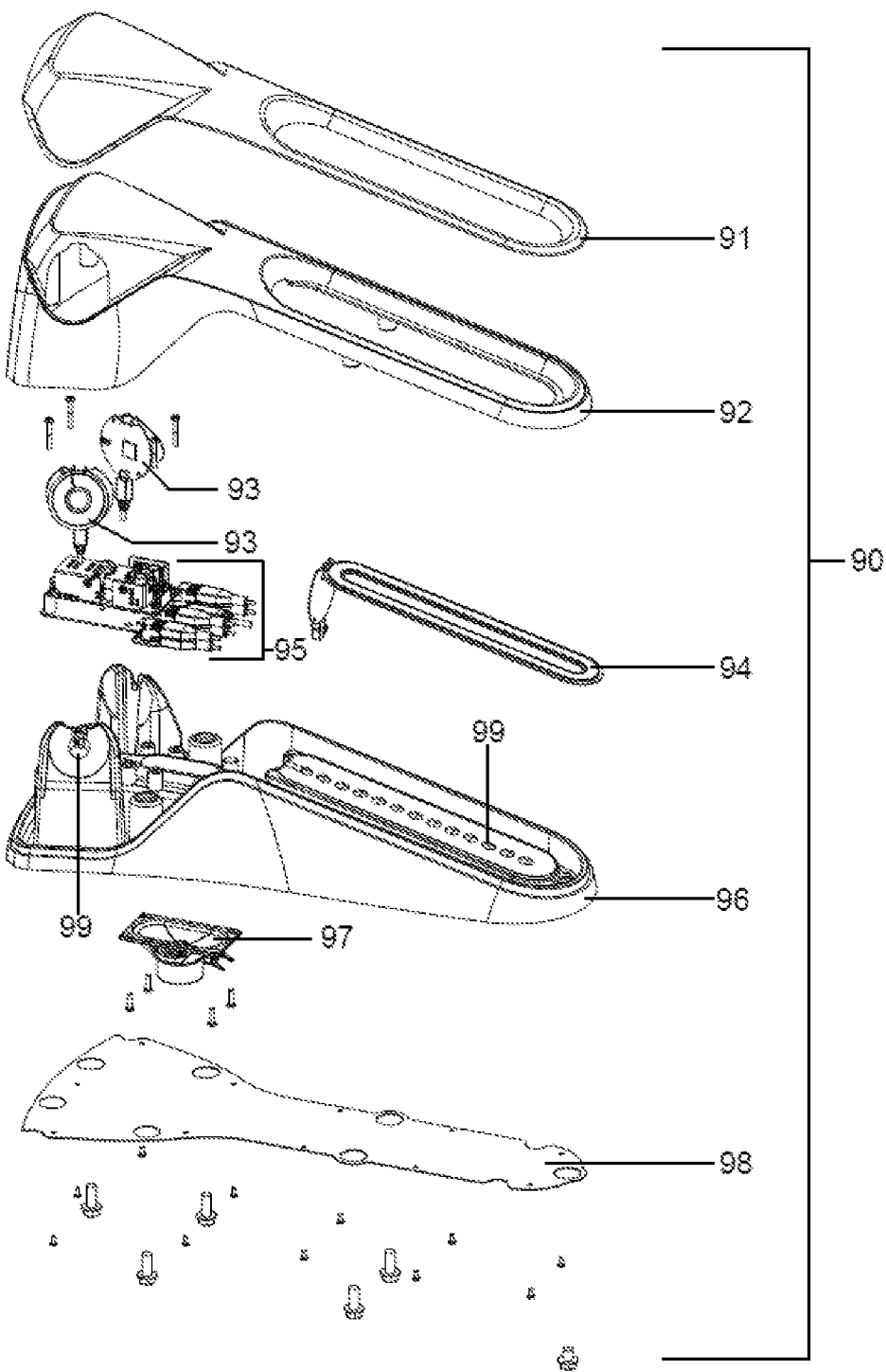
FIG. 8 depicts an exploded view of a sensor base.

The base unit 90, as depicted in FIGS. 7 and 8, provides for several features for the SDD, including charging of the sensor pods, quality control of the sensor pods, and calibration of the sensor pods.

The base unit 90 charges the sensor pods 1 through induction charging. Accordingly, each pod 1 comprises a receptor for receiving charge through the induction charging devices placed within a cradle in the base unit 90. FIG. 7 depicts a sensor array 5 arranged onto a base 90, and replaceable sensor pads 80 adjacent to the base 90. The base 90 provides for several features for the array 5 including charging of the sensor pods 1, quality control of the sensor pods 1, and calibration of the sensor pods 1. In one embodiment, the base 90 and/or the sensor pods 1 have a charge indicator that indicates when charging is occurring. Additionally, the charge indicator preferably indicates when charging is complete. FIG. 7 shows the array 5 removed from the base 90, however the base 90 defines several cradles, or indentations, for accepting the sensor pods 1 when the array 5 is placed onto the base.

The base 90 charges the sensor pods 1 via inductive charging. Accordingly, each sensor pod 1 comprises a receptor, wireless charging coil, for receiving a charge from an induction-charging device in the base 90. Alternatively, the array 5 can have a charging contact and the base 90 can have a corresponding charging contact to provide charging power to the sensor pods 1.

Further disposed of within the base unit, and specifically adjacent to the cradle for each of the sensor pods, is a speaker 97. The speaker 97 is engaged to the computer, and when the SDD is engaged, a program running through the computer system performs a diagnostic and quality control program on each of the sensor pods.

FIG. 8 depicts an exploded view of the base 90 that provides charging and calibration for the array 5. The base 90 comprises a base enclosure top 92, a base enclosure bottom 96, and a bottom closure plate 98. A decorative elastomeric TPE over-mold 91 can be provided to protect the base 90 and the array 5. Arranged in the base 90 are an electronic module 95 and wireless charging coils 93, 94. The wireless charging coils 93, 94 are arranged to power the respective wireless charging coils 67 of the sensor pods 1. Also arranged in the base 90 is a calibration speaker 97. The electronic module 95 powers the wireless charging coils 93, 94. In one embodiment, the electronics module generates a calibration and verification signal to be reproduced by the calibration speaker 97. The base enclosure bottom 96 has one or more sound holes 99 arranged therein.

In one embodiment, disposed of within the base 90, and specifically adjacent to the cradle for each of the sensor pods 1, is a respective speaker 97. A computer is coupled to the base 90 for communication via a USB connection, Bluetooth, near field communication, RS-232, or the like. The computer couples to the speaker 97, and when the SDD is engaged, a program is executed by the computer system so that it performs a diagnostic and quality control test on each of the sensor pods 1.

The diagnostic and quality control procedure comprises a program that plays a known set of sounds corresponding to sounds that will be detected and recorded when measuring sounds on the body of a patient. These sounds include low and high frequency sounds, typically at amplitudes to mimic the sounds generated by the carotid arteries. Once the sounds are played, the sensor pods detect the sounds and convert the sound to digital where it is matched up to a predetermined plot of the sounds that are to be played. Each of the sensor pods is independently determined to meet an acceptable standard.

If any of the sensor pods are not detecting an appropriate sound, then the system will notify the user of an error. In most instances, the error means that the particular sensor pod has spent its useful lifetime and is due for replacement. While these devices may theoretically have a lifespan of several hundred uses, under perfect conditions, the reality of a medical office and placing a device on or adjacent to a patient and detecting and recording real sounds may cause distortion after even a few uses. Accordingly, the system is able to detect whether the sounds detected are simply drift that is a slight change in the detected sounds or whether there is an error or fault in one of the sensors. If there is only a slight drift, the system can calibrate each unit so that the measured noises from the system are consistent through use.

If the measured sounds are greater than a slight drift, i.e. greater than about 5% with regard to the wavelength and the amplitude, the system engages the user through images on the display, lights on the sensor pod, audible messages, or other means for communicating error, and wherein the particular sensor pod that is faulty is identified. An appropriate error range includes between about 0.1 to about 20% for this quality control provision. A user can then quickly replace the faulty sensor pod, which is a disposable and replaceable component and re-run the quality control program from the start. After the sensor pod is replaced and the quality control program is re-run, and the replacement sensor pod is confirmed to be working properly, the system will alert that it is ready for placing on a patient. Each of the sensor pods can be appropriately placed onto the patient.

Accordingly, in a further embodiment, the method further comprises a step of performing a quality control procedure on the device once the device is placed on a patient. This quality control step is necessary because where the sensors are not in the correct location on the body a weak or improper signal may distort data or provide inaccurate results. This is a critical issue for an operator and user, as improper signals would generate potentially inaccurate results.

Where testing is of the carotid artery, one sensor pod is placed adjacent to the heart and at least one sensor pod is placed adjacent to either the left or right carotid artery. In preferred embodiments, a sensor pod is placed adjacent to both the left and the right carotid artery. As with the quality control procedure on the base unit, once the sensor pods are placed on the patient, the operator can engage the SDD system to begin detection and recording on the patient. Because the sounds that are being detected and recorded are known, that is, the sounds are generally known to a certain frequency and amplitude, for a duration of between 5 and 30 seconds, the SDD system performs a further sensor pod quality control diagnostic to ensure that the sensor pods are detecting proper sounds from the patient.

Since there are at least two and likely three sensor pods, each pod communicates with the computer identifying the detected sounds, which can be recorded by the system and compared in real time to a predicted sound. Accordingly, the sensor pod at the heart will predict a certain sound and the sensor pod(s) at the carotid arteries another sound. If one or more sensors does not detect the predicted sounds, a signal will engage to identify the sensor that is not properly detecting the predicted sound. This signal will alert the operator that the sensor pod needs to be adjusted to a different position to properly detect the sounds for the particular test. After the adjustment, the operator can then re-start the quality control procedure after modifying the position of the one or more arrays on the person. Where the quality control test confirms appropriate position, typically a variance of about less than 25%, the system can automatically begin to detect and record data. Preferred variances to the wavelength and amplitude are between about 0.1% to about 40% for this test. Typically, a full test is performed from between 30 to 120 seconds, where data is detected and sent to the computer and stored for analysis.

Therefore, quality control measures are necessary to ensure that the CDD is performing properly for each test. Indeed, the quality control steps ensure that the sensor pods are ready to detect from a patient the vortex motions. The vortex motions in the carotid artery exist in a range between about 40 to about 1600 Hz, with the most relevant range between about 60 and about 1200 Hz. Accordingly, the system detects and records sounds from the carotid artery and the heart and captures and stores all the sounds detected. However, sounds above and below the 40 and 1600 Hz range are removed from the data as an initial step in cleaning the data. Of course, there is a litany of other sounds detected and recorded by the sensor pods. Accordingly, there is a need to filter and remove unnecessary sounds to assist in identifying the specific sounds related to the vortices.

Figure 5:
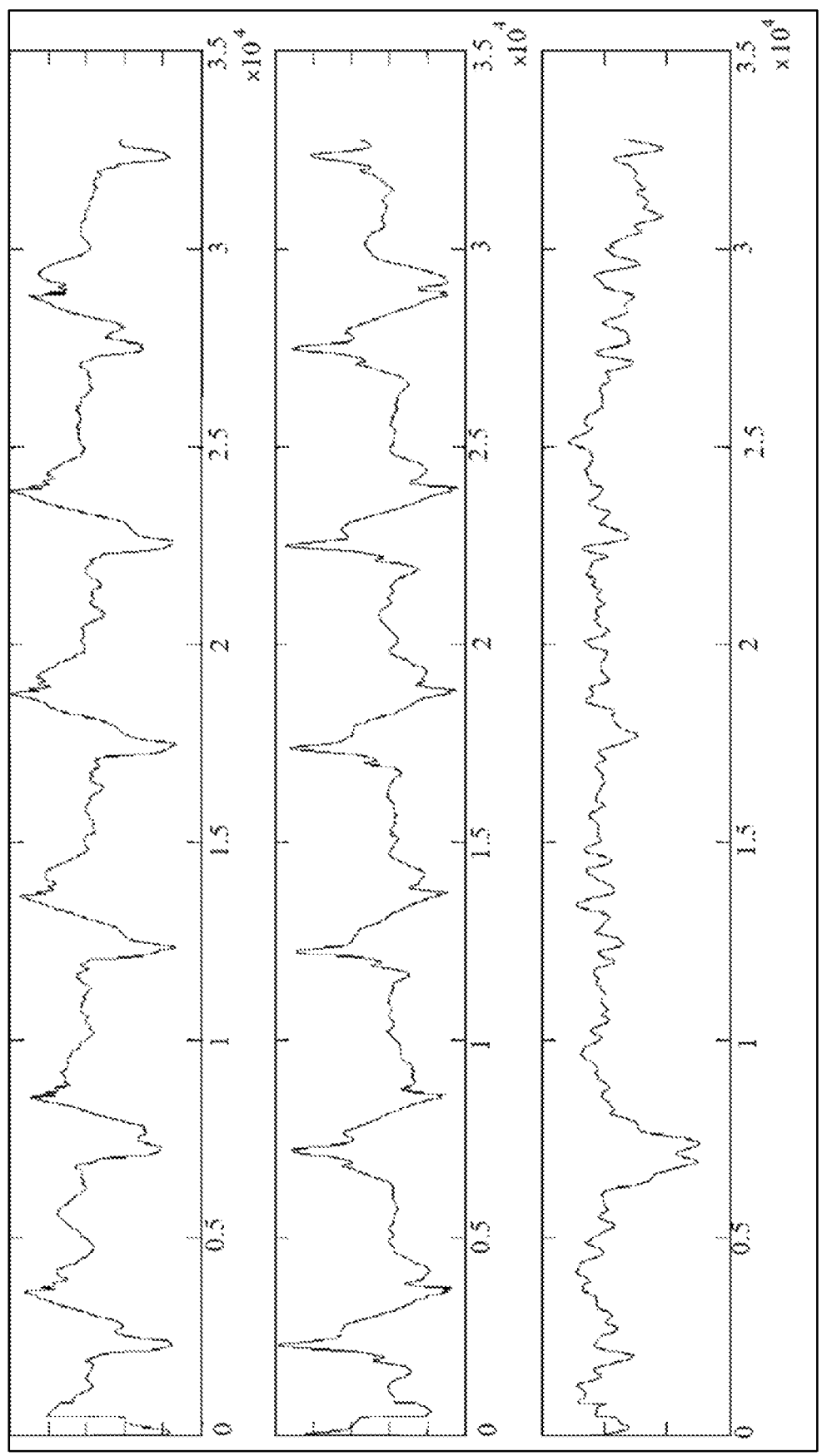
FIG. 5 depicts a representative set of data collected from the carotid stenosis device. Top figure: Left carotid artery. Middle figure: Right carotid artery. Bottom figure: From sensor placed on the sternum. All three were measured simultaneously and a total of seven heartbeats are shown.

FIG. 5 depicts images showing an example of the data received and recorded by the sensor pods. The image on the left shows jagged data along the plot, while the right hand image provides a best-fit line for the data. Therefore, a further step comprises de-noising the data by removing sounds outside of the 40-1600 Hz region. Removal of these sounds through several filtering programs provides for cleaner data that is then utilized for generation of power spectral density graphs. The filtered sound is preferably filtered using Discrete Wavelet Transform processes. This results in clean data that can be appropriately graphed for further processing. The data that is processed and de-noised includes a larger range of sounds than is typically relevant for the vortices. However, to ensure capture of all relevant data, when generating a cut-off for removal of unnecessary data, and to graphically identify a power spectral density graph, the greater range of 40-1600 Hz is used, when typically only the range of 60-1200 Hz is relevant for our purposes.

Figure 6:
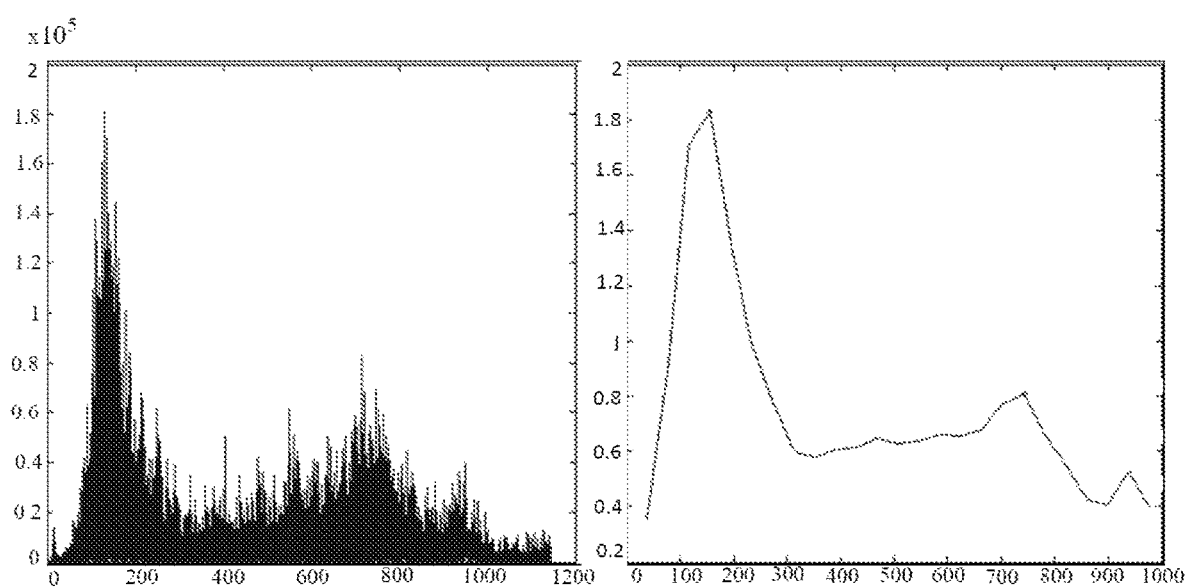
FIG. 6 is a representative Power Spectral Density graph, showing raw spectral data on the left and smoothed data on the right.

A comparison between clean data and raw data is provided in FIG. 6, wherein the image on the left hand side provides for raw data, wherein the data on the right hand side is data that has been filtered and smoothed. Smoothed data generates a clean best-fit style line over the data generated at a particular Hz.

Indeed, the cleaned data is thereafter utilized to generate a Power spectral display. The Power Spectral Display generates a graphical representation of peaks detected from the vortices to determine the frequencies of largest amplitude from between 60-1200 Hz. For example, FIG. 6 depicts a representative power spectral density graph. These peaks, for example, on the right hand side, are then utilized for determination of stenosis of the carotid artery.

A step in the process takes analog sounds and transforms the analog to digital. When the sounds detected are transformed from analog to digital, the analog signal was down sampled using a sampling rate of 20 kHz. Appropriate ranges of down sampling may be utilized in other embodiments as is known to one of ordinary skill in the art.

In further embodiments, it is necessary to filter the recorded sound to eliminate noise from the data. The sensing pods are highly sensitive to sound and thus capture many noises that are not relevant to the vortices. Therefore, the embodiments utilize pre-determined cut-off values to remove sounds falling outside of the range of 40 Hz to about 1600 Hz.

In a preferred method for detecting and measuring vortices in the carotid artery, the method comprises a seven-step process:

(1) The device first goes through a series of quality control steps, in concert with the device. In particular, the system plays a predetermined set of tones that are detectable by the sensor pods, and the system compares what is detected by the sensor pods to the actual tones played by the system. After confirmation of proper function, the device is ready to place on a patient. Where any sensor pod is identified as faulty, replacement is warranted before re-running the first quality control step.

(2) Placing at least two sensor pods on a patient, one adjacent to the heart and one adjacent to a carotid artery. Thus, the sensor pods are positioned for capture of sounds on a body.

(3) A second quality control process is performed once the sensor pods are placed adjacent to the artery of interest and the heart, wherein the quality control process ensures correct receipt of the signals to the sensor elements, correlating the signals from the two carotid arteries and the heart, and identifying the systolic time—the period of most rapid fluid flow. The system compares the detected sounds to a predetermined set of sounds that are expected to be detected from the heart and the carotid arteries. Confirmation of these sounds will automatically start the test, or the test can be started by the press of a button by an operator. Rejection of the placement of the sensor pods will generate an alert, wherein the operator can revise the position of one or more sensor pods and the re-start the second quality control process.

(4) Detecting and recording sounds from the heart and carotid artery for between 30 seconds and 120 seconds so as to gather data for processing. This step converts the sound from analog to digital using a down sampling rate of 20 kHz. Other optional conversion mechanisms may be utilized or various sampling rates known to one of ordinary skill in the art, including sampling rates from 10 Hz to 32 kHz.

(5) Once the sounds are recorded, the system prepares the data for processing the digital signal to conduct a spectral analysis.

(6) Cleaning the data by performing a cleansing of data outside of the range of 40 Hz to 1600 Hz. Furthermore, optional additional cleansing processes may be used including utilization of wavelet analysis for cleaning the data.

(7) Finally, the data is cleaned and the system generates a power spectral density graph of the cleaned data.

In further embodiments, a further eighth (8) step is to quantify stenosis in the artery based on the power spectral density graph. Indeed, the data can be utilized in conjunction with statistical analysis performed against multiple parameters to render a classification of degree of stenosis within each carotid artery. The output renders a report indicating the level of stenosis as a percent occlusion.

FIG. 3, as previously addressed, provides for a simplified flow-process of detection of vortices in the carotid artery, which consists of the follow steps: First the data is sampled from the patient 100 and the sound/vibrations are converted from analog to digital 101. The data is streamed from the device and stored as a digital file containing sounds from three channels, the heart and, left and right carotid arteries 102. The data is captured in three streams, one for the left sensor and one for the right and one for the heart and are analyzed 103; in particular, noise is removed from the data. A power spectral density analysis is performed wherein a power spectral density (PSD) 104 is generated. The PSD identifies the frequencies of noise found within the data and how strong/powerful the noise is and graphing the PSD defines one or more peaks on a graph. A further embodiment consists of a further step wherein the correlation between the peaks thereafter determines the amount of stenosis present in the patient. Additional embodiments may comprise further steps in the processes as described herein.

Arteries that contain smooth walls and no buildup of cholesterol, or other debris or materials deposited on the walls of the artery are common in children and young adults. However, certain hereditary issues and lifestyle choices may induce the gradual buildup of materials along the artery walls that can ultimately lead to complete block of the artery over time. Upon formation of some buildup of material along the wall, and certainly as blockage of more than 50% or more than 70 or 90% of the artery occurs, two or more peaks are present in the PSD. See FIG. 6, which identifies several peaks that correlate to stenosis in the carotid artery.

Therefore, a method for determining stenosis of the carotid artery in a human patient consists of a first step of placing a sensing device comprising an array and three sensing elements onto the patient, wherein a first sensing element is placed near the heart and the two remaining sensing elements are placed adjacent to the carotid arteries; the sensing elements then measure sounds from each of the three sensing elements, resulting in sound from three channels. The sound is measured in analog and modified to digital format and then each of the three channels are analyzed before a power spectral density analysis is performed. The power spectral density graph reveals peaks that are then analyzed to provide for a calculation of percent stenosis or occlusion of the carotid artery.

What is claimed is:

1. A method for measuring sound from vortices in the carotid artery comprising:
   a. performing a first quality control procedure on an array comprising at least two sensing elements, said array stored on a base unit, wherein said quality control procedure is performed by playing a pre-determined set of tones within said base unit, wherein said at least two sensing elements detect said set of tones and wherein said detected tones are compared to said pre-determined set of tones;
   b. after step (a), performing a second quality control procedure on the at least two sensing elements, wherein said second quality control procedure is performed by detecting sounds generated by the heart and by blood flow through the carotid artery; wherein said at least two sensing elements detect said sounds generated by the heart and blood flow through the carotid artery, and said detected sounds are compared to a previously recorded set of sounds corresponding to the sounds generated by the heart and blood flow through the carotid artery;
   c. after step (b), detecting sounds generated by the heart and sounds from vortices in the carotid artery for at least 30 seconds.

2. The method of claim 1, wherein the sounds detected from the vortices in the carotid artery are between 40 Hz and 1600 Hz.

3. The method of claim 1, wherein a further step (d) comprises eliminating sounds from the carotid artery that are outside of the range of 40 Hz and 1600 Hz.

4. The method of claim 3, comprising a further step (e) comprising generating a power spectral density graph of the sounds from step (d).

5. The method of claim 1 comprising three sensor pods.

6. The method of claim 1 wherein in step (a), wherein if the comparison between said detected tones and said pre-determined tones has a variance of more than 5% relative to the amplitude or wavelength, then the sensing element is determined to be faulty.

7. The method of claim 1, wherein in step (b), if the detected sounds compared to the previously recorded sounds have a variance of more than 25% relative to the amplitude, then the sensing elements need to be repositioned.

* * * * *